United States Patent
Zimmermann et al.

(10) Patent No.: US 6,846,910 B2
(45) Date of Patent: Jan. 25, 2005

(54) ISOLATED PROTEINS CONTAINING PORTIONS OF FAPα AND OTHER PROTEINS

(75) Inventors: Rainer Zimmermann, Mittelbiberach (DE); John E. Park, Biberach (DE); Wolfgang Rettig, Biberach (DE); Lloyd J. Old, New York, NY (US)

(73) Assignees: Ludwig Institute for Cancer Research, New York, NY (US); Boehringer Ingelheim International GmbH, Ingelheim em Rhein (DE)

(*) Notice: Subject to any disclaimer, the term of this patent is extended or adjusted under 35 U.S.C. 154(b) by 108 days.

(21) Appl. No.: 09/265,606

(22) Filed: Mar. 10, 1999

(65) Prior Publication Data

US 2002/0034789 A1 Mar. 21, 2002

Related U.S. Application Data

(60) Division of application No. 08/940,391, filed on Oct. 1, 1997, now Pat. No. 5,965,373, which is a continuation-in-part of application No. 08/230,491, filed on Apr. 20, 1994, now Pat. No. 5,587,299.

(51) Int. Cl.[7] .................. C07K 14/745; C07K 14/52; C07K 19/00

(52) U.S. Cl. .................... 530/381; 530/351; 424/192.1
(58) Field of Search ................. 530/381, 351; 424/192.1

(56) References Cited

PUBLICATIONS

Niedermeyer et al. Mouse fibroblast–activation protein. European Journal of Biochemistry (Jun. 1998) vol. 254 (2), pp. 650–654.*

Ogata et al. Identification of the ative site residues in dipeptidyl peptidase IV by affinity labeling and site–directed mutagenesis. Biochemistry, vol. 31, pp. 2582–2587 (1992).*

Geysen et al. Cognitive features of continuous antigenic determinants. (J. of Molecular Recognition, vol. 1, pp. 32–40, 1988).*

Rettig et al. Cancer Research, vol. 53, pp. 3327–3335, 1993.*

* cited by examiner

Primary Examiner—Marjorie Moran
(74) Attorney, Agent, or Firm—Fulbright & Jaworski L.L.P.

(57) ABSTRACT

The invention involves dimeric forms of the protein known as fibroblast activation protein alpha, or "FAPα" and its uses.

5 Claims, 3 Drawing Sheets

FIG. 1

```
FAP    1 MKTWVKIVFGV*ATSAVLALLVKCIVLRPSRVHNSEEKTMRALTLKDILN   49
CD26   1 ---PW-VLL-LLGAA-LVTIITVPV--LNKGTDDATADSRKTY--T-Y-K   50

FAP   50 GTFSYKTFFPNWISGQEYLHQSADNNIVLYNIETGQSYTILSNRTMKSV*   98
CD26  51 N-YRL-LYSLR---DH---YKQ*E---LVF-A-Y-N-SVF-E-S-FDEFG   99

FAP   99 *NASNYGLSPDRQFVYLESDYSKLWRYSYTATYYIYDLSNGEFVRGNELP  147
CD26 100 HSIND-SI---G--IL--YN-V-Q--H----S-D----NKRQLITEERI-  149
                                                     fap-1
FAP  148 RPIQYLCWSPVGSKLAYVVYQNNIYLKQRPGDPPFQITFNGRENKIFNGIP 197
CD26 150 NNT-WVT-----H-----WN-D--V-IE-NL-SYR--WT-K-DI-Y---T  199
                    fap-2
FAP  198 DWVYEEEMLPTKYALWWSPNGKFLAYAEFNDKDIPVIAYSYYGDE**QYP  245
CD26 200 -------VFSAYS--------T-----Q---TEV-L-E--F-S--SL---  249

FAP  246 RTINIPYPKAGAKNPVVRIFIIDT***TYPAYVGPQEVPVPAMIASSDYY  292
CD26 250 K-VRV------V--T-KF-VVN-DSLSSVTNATSIQITA--SMLIG-H-  299

FAP  293 FSWLTWVTDERVCLQWLKRVQNVSVLSICDFREDWQTWDCPKTQEHIEES  342
CD26 300 LCDV--A-Q--IS----R-I--Y--MD---YD-SSGR-N-LVARQ---M-  349

FAP  343 RTGWAGGFFVSRPVFSYDAISYYKIFSDKDGYKHIHYIKDTVENAIQITS  392
CD26 350 T---V-R-RP-E-H-TL-GN-F---I-NEE--R--C-FQIDKKDCTF--K  399

FAP  393 GKWEAINIFRVTQDSLFYSSNEFEEYPGRRNIYRISIGSYPPSKKCVTCH  442
CD26 400 -T--V-G-EAL-S-Y-Y-I---YKGM--G--L-K-QLSD-T*KVT-LS-E  448

FAP  443 LRKERCQYYTASFSDYAKYYALVCYGPGIPISTLHDGRTDQEIKILEENK  492
CD26 449 -NP------SV---KE----Q-R-S---L-LY---SSVN-KGLRV--D-S  498
                                          fap-3
FAP  493 ELENALKNIQLPKEEIKKLEVDEITLWYKMILPPQFDRSKKYPLLIQVYG  542
CD26 499 A-DKM-Q-V-M-SKKLDFIILN-TKF--Q-----H--K-------LD--A  548

FAP  543 GPCSQSVRSVFAVNWISYLASKEGMVIALVDGRGTAFQGDKLLYAVYRKL  592
CD26 549 -----KADT--RL--AT----T-NIIV-SF----SGY----IMH-IN-R-  598

FAP  593 GVYEVEDQITAVRKFIEMGFIDEKRIAIWGWSYEIRFITGPCIWNWSFQM  642
CD26 599 -TF------E-A-Q-SK---V-N---------GGYVTSMVLGSGSVGFK  648

FAP  643 WYSSGSSLQLGILRVCLHRE*IHGSPNKDDNLEHYKNSTVMARAEYFRNV  691
CD26 649 CGIAVAPVSRWEYYDSVYT-RYM-L-TPE---D--R-----S---N-KQ-  698

FAP  692 DYLLIHGTADDNVHFQNSAQIAKALVNAQVDFQAMWYSDQNHGLSGLSTN  741
CD26 699 E--------------Q----S----DVG--------T-ED--IASSTAH  748

FAP  742 *HLYTHMTHFLKQCFSLSD
CD26 749 Q-I----S--I------P
```

FIG. 2

| | Breast Cancer | MFH | Healing Wound | Renal Cancer |
|---|---|---|---|---|
| FAPα | ⊕<br>A | ⊕<br>C | ⊕<br>E | ⊖<br>G |
| CD26 | ⊖<br>B | ⊖<br>D | ⊕<br>F | ⊕<br>H |

Immunohistochemistry (See Kodachromes)

ISOLATED PROTEINS CONTAINING PORTIONS OF FAPα AND OTHER PROTEINS

RELATED APPLICATION

This application is divisional of Ser. No. 08/940,391 filed Oct. 1, 1997 now U.S. Pat. No. 5,965,373 which a continuation-in-part of Ser. No. 08/230,491, filed Apr. 20, 1994 now U.S. Pat. No. 5,587,299.

FIELD OF THE INVENTION

This invention relates to certain molecules associated with cancer tissues and reactive tumor stromal cells. More particularly, it relates to fibroblast activation protein alpha ("FAPα" hereafter) molecules. A monomeric form of the molecule has previously been identified immunochemically, but nucleic acid molecules coding for it had not been isolated or cloned nor have dimers been identified. These, inter alia, are features of the invention. The monomeric protein has a molecular weight of from about 88 to about 95 kilodaltons as determined by SDS-PAGE of boiled samples. The dimer has a molecular weight of about 170 kilodaltons as determined by SDS-PAGE of unboiled samples. FAPα is characterized by a number of features and properties which are shared by and characteristic of membrane bound enzymes, suggesting very strongly that it, too, is a membrane bound enzyme. The nucleic acid molecules, which are a key part of the invention, are useful both as probes for cells expressing FAPα, and as starting materials for recombinant production of the protein. The FAPα protein can then be used to produce monoclonal antibodies specific for the protein and are thus useful diagnostic agents themselves. They also have additional uses, including uses related to enzymatic functions, as described herein.

BACKGROUND AND PRIOR ART

The invasive growth of epithelial cancers is associated with characteristic cellular and molecular changes in the supporting stroma. For example, epithelial cancers induce the formation of tumor blood vessels, the recruitment of reactive tumor stromal fibroblasts, lymphoid and phagocytic infiltrates, the release of peptide mediators and proteolytic enzymes, and the production of an altered extracellular matrix (ECM). See, e.g., Folkman, Adv. Cancer Res. 43: 175–203 (1985); Basset et al., Nature 348: 699–704 (1990); Denekamp et al., Cancer Metastasis Rev. 9: 267–282 (1990); Cullen et al., Cancer Res. 51: 4978–4985 (1991); Dvorak et al., Cancer Cells 3: 77–85 (1991); Liotta et al., Cancer Res. 51: 5054s-5059s (1991); Garin-Chesa et al., J. Histochem. Cytochem. 37: 1767–1776 (1989). A highly consistent molecular trait of the stroma in several common histologic types of epithelial cancers is induction of the fibroblast activation protein (FAPα), a cell surface glycoprotein with an observed $M_r$ of 95,000 originally discovered with a monoclonal antibody, mAb F19, raised against proliferating cultured fibroblasts. See Rettig et al., Cancer Res. 46: 6406–6412 (1986); Rettig et al., Proc. Natl. Acad. Sci. USA 85: 3110–3114 (1988); Garin-Chesa et al., Proc. Natl. Acad. USA 87: 7235–7239 (1990); Rettig et al., Cancer Res. 53: 3327–3335 (1993). Each of these four papers is incorporated by reference in its entirety.

Immunohistochemical studies such as those cited supra have shown that FAPα is transiently expressed in certain normal fetal mesenchymal tissues but that normal adult tissues are generally FAPα−. Similarly, malignant epithelial, neural and hematopoietic cells are generally FAPα−. However, most of the common types of epithelial cancers, including >90% of breast, lung, skin, pancreas, and colorectal carcinomas, contain abundant FAPα+ reactive stromal fibroblasts. Garin-Chesa et al., Proc. Natl. Acad. Sci. USA 87: 7235–7239 (1990). The FAPα+ tumor stromal fibroblasts almost invariably accompany tumor blood vessels, forming a distinct cellular compartment interposed between the tumor capillary endothelium and the basal aspect of malignant epithelial cell clusters. While FAPα+ stromal fibroblasts are found in both primary and metastatic carcinomas, benign and premalignant as epithelial lesions, such as fibroadenomas of the breast and colorectal adenomas only rarely contain FAPα+ stromal cells. In contrast to the stroma-specific localization of FAPα in epithelial neoplasms, FAPα is expressed in the malignant cells of a large proportion of bone and soft tissue sarcomas. (Rettig et al., Proc. Natl. Acad. Sci. USA 85: 3110–3114 (1988)). Finally, FAPα+ fibroblasts have been detected in the granulation tissue of healing wounds (Garin-Chesa et al., supra). Based on the restricted distribution pattern of FAPα in normal tissues and its uniform expression in the supporting stroma of many epithelial cancers, clinical trials with $^{131}$I-labeled mAb F19 have been initiated in patients with metastatic colon cancer (Welt et al., Proc. Am. Assoc. Cancer Res. 33: 319 (1992); Welt et al. J. Clin. Oncol. 12: 1561–1571 (1994)) to explore the concept of "tumor stromal targeting" for immunodetection and immunotherapy of epithelial cancers.

Rettig et al., Int. J. Cancer 58: 385–392 (1994), incorporated by reference, discusses the FAPα molecule and its features. Rettig et al postulate that FAPα is found in high molecular weight complexes in excess of 400 kilodaltons, but do not discuss the possibility of dimeric molecules, nor does the paper elaborate on the specific enzymatic properties of the molecule.

The induction of FAPα+ fibroblasts at times and sites of tissue remodeling during fetal development, tissue repair, and carcinogenesis is consistent with a fundamental role for this molecule in normal fibroblast physiology. Thus, it is of interest and value to isolate and to clone nucleic acid molecules which code for this molecule. This is one aspect of the invention, which is described in detail together with other features of the invention, in the disclosure which follows. Further aspects of the invention include the dimeric FAPα molecules, and the exploitation of the properties of these molecules. These features are also elaborated upon hereafter.

BRIEF DESCRIPTION OF THE FIGURES

FIG. 1 compares the deduced amino acid sequence for FAPα, and the known sequence of CD26. The alignment has been optimized.

FIGS. 2A–2H, inclusive, display immunohistochemical detection of FAPα and CD26 in various tissues. In FIGS. 2A and 2B, breast cancer is studied, for FAPα (FIG. 2A), and CD26 (FIG. 2B). In FIGS. 2C and 2D, malignant fibrous histiocytoma is studied, for FAPα (FIG. 2C), and CD26 (FIG. 2D). Dermal scar tissue is examined in FIGS. 2E (FAPα), and 2F (CD26). Renal cell carcinoma is studied in FIGS. 2G (FAPα), and 2H (CD26).

DETAILED DESCRIPTION OF PREFERRED EMBODIMENTS

EXAMPLE 1

Figure 3:
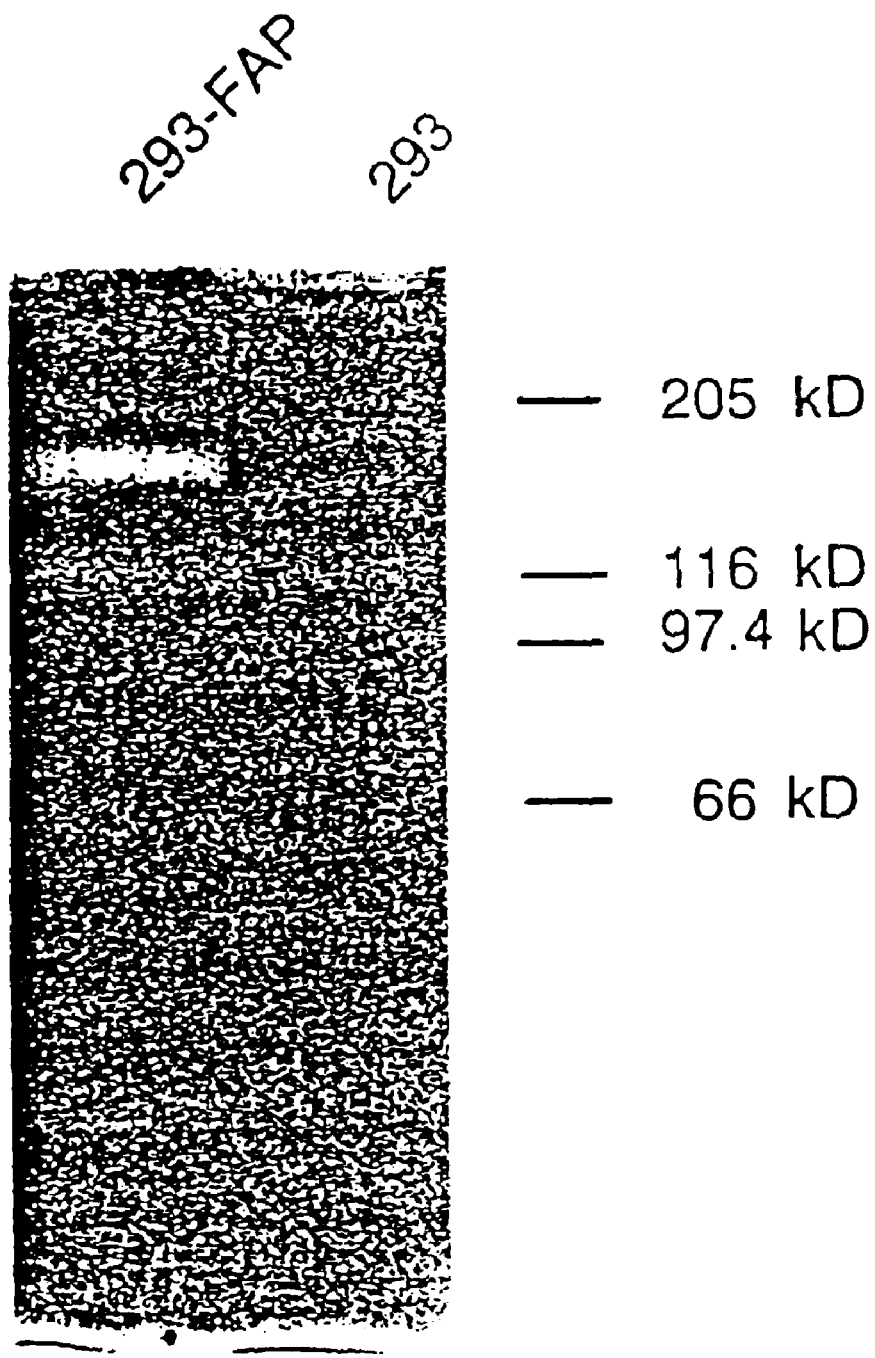
FIG. 3 presents some of the data generated in experiments which showed that FAPα had extracellular matrix (ECM) protein degrading activity. When zymographic detection of gelatin degrading extracts of 293-FAP was carried out, the active substance was found to have a molecular weight of about 170 kD, via SDS-PAGE, using unboiled samples to preserve enzyme activity.

Fibroblast cell line WI-38 had been observed, previously, to react with mAb F19 (Rettig et al., Canc. Res. 46: 6406–6412 (1986); Rettig et al., Proc. Natl. Acad. USA 85: 3110–3114 (1988); Garin-Chesa et al., Proc. Natl. Acad. Sci. USA 87: 7235–7239 (1990); Rettig et al., Canc. Res. 53: 3327–3335 (1993)). It was used in the experiments which follow.

A cDNA library was prepared from WI-38, using well known techniques and commercially available materials. Specifically, the library was constructed in expression vector pCDNAI, using the Fast Track mRNA isolation kit, and Librarian cDNA phagemid system. Once the library was prepared, the vectors were electroporated into cell line *E. coli* MC 1061/P3. The pCDNAI expression vector contains an antibiotic resistance gene, so the *E. coli* were selected via antibiotic resistance. The colonies which were resistant were then used in further experiments. The plasmid DNA from the colonies was obtained via alkaline lysis and purification on $CsCl_2$, in accordance with Sambrook et al, Molecular Cloning: A Laboratory Manual (Cold Spring Harbor Lab, Cold Spring Harbor, N.Y. 2d Ed. 1989). The technique is well known to the art, but is incorporated by reference herein.

Once the plasmid DNA was isolated, it was used to transfect COS-1 cells, which were then cultured for forty-eight hours, after which these were tested with antibody coated dishes. The mAbs used included F19, as described by Rettig et al., (1986), supra, which is incorporated by reference in-its entirety. As COS-1 cells are normally $FAP\alpha^-$, any positive results indicated the presence of the coding sequence. The immunoselection protocol was that of Aruffo et al., Proc. Natl. Acad. Sci USA 84: 3365–3369 (1987), incorporated by reference herein.

Plasmid DNA from positive clones was recovered, in accordance with Hirt, J. Mol. Biol. 26: 365–369 (1967), reintroduced into *E. coli* MC 1061/P3, and reselected in COS-1 cells.

The protocol presented herein was followed for four rounds. After this, the plasmid DNA of 50 isolated bacterial colonies was purified, using the Qiagen plasmid kit. Of the colonies, 27 clones were found to contain identical 2.8 kb inserts, as determined by EcoRI restriction enzyme mapping. Several of these were found to contain $FAP\alpha$-specific cDNA as determined by transient expression in COS-1 cells and direct immunofluorescence staining with mAb F19. One of these clones, i.e., "pFAP.38" was selected for further study, as elaborated upon infra.

EXAMPLE 2

Once pFAP.38 had been identified, it was tested together with a vector coding for known cell surface marker CD26 ("pCD26"), as well as with control vector pCDNA I.

In these experiments, COS-1 cells were transfected with one of pFAP.38, pCD26, or pCDNAI. After forty-eight hours, the transfectants were tested, using the well known MHA rosetting assay for cell surface antigen expression. In these experiments, mAb F19, which is $FAP\alpha$ specific, was used, together with mAb EF-1, which is CD26 specific. Also used were four other $FAP\alpha$ specific mAbs, i.e., FB23, FB52, FB58 and C48. Also tested were two cancer cell lines, which are known to react with mAb F19 (SW872 liposarcoma), or EF-1 (SK-OV6 ovarian cancer). The results are set forth in Table 1, which follows.

TABLE 1

Cell surface expression of multiple $FAP\alpha$ epitopes and CD26 in human cells and COS-1 cell transfectants

| Target cell | Cell surface antigen expression | | | | | |
|---|---|---|---|---|---|---|
| | F19 | FB23 | FB52 | FB58 | C48 | EF-1 |
| Human cells | | | | | | |
| SW872 liposarcoma | >95% | >95% | >95% | >95% | >95% | — |
| SK-OV6 ovarian cancer | — | — | — | — | — | >95% |
| COS-1 transfectants | | | | | | |
| COS . pCDNAI control | — | — | — | — | — | — |
| COS . pFAP 38 | 40% | 30% | 40% | 20% | 20% | — |
| COS . pCD26 | — | — | — | — | — | 40% |

SEQ ID NO:10

EXAMPLE 3

Immunoprecipitation studies were then carried out to identify the antigen being targeted by the antibodies.

Cells were metabolically labelled with Trans $^{35}$S-label, (ICN), extracted with lysis buffer (0.01M Tris-HCl/0.15M NaCl/0.01M $MgCl_2$/0.5% Nonidet P-40/aprotinin (20 ug/ml)/2 mM phenylmethyl-sulf onyl fluoride), and then immunoprecipitated. The protocols used are all well known, as will be seen by reference to Rettig et al., Canc. Res. 53: 3327–3335 (1993); and Fellinger et al., Canc. Res. 51: 336–340 (1991), the disclosures of which are all incorporated by reference in their entirety. Precipitating mAbs were negative control mouse Ig, mAb F19, or EF-1. Control tests were carried out with mock transfected COS-1 cells. Following immunoprecipitation, the immunoprecipitates were boiled in extraction buffer and separated by $NaDodSO_4$/PAGE, under reducing conditions. In some experiments, an additional test was carried out to determine whether or not the immunoprecipitated material was glycosylated. In these experiments, cell extracts were fractionated with Con A-SEPHAROSE prior to immunoprecipitation. Following immunoprecipitation, but prior to fractionation on $NaDodSO_4$/PAGE, these precipitates were digested with N-Glycanase.

The results showed that, in COS-1 cells, pFAP.38 directs expression of an 88 kd protein species (as determined via SDS-PAGE), which is slightly smaller than the 95 kd $FAP\alpha$ species produced by SW872, or cultured fibroblasts. Digestion with N-Glycanase produced peptides of comparable size (i.e., 74 kd versus 75 kd), showing that the glycosylation of the FAPA protein in COS-1 cells is different than in the human cell lines.

EXAMPLE 4

Classic Northern blot analysis was then carried out, using the mRNA from $FAP\alpha^+$ fibroblast cell lines WI-38 and GM 05389, and $FAP\alpha^-$ ovarian cancer cell line SK-OV6. Using the procedures of Sambrook et al., supra, five micrograms of mRNA from each cell line were tested. The probes used were $^{32}$P labelled, and were prepared from a 2.3 kb ECO I fragment of pFAP.38, a 2.4 kb Hind III fragment of CD26, and a 1.8 kb BamHI fragment of γ-actin cDNA. These fragments had been purified from 1% agarose gels.

The extracts of $FAP\alpha^+$ fibroblast strains showed a 2.8 kb FAP mRNA species, but extracts of SK-OV6 do not. A γ-actin mRNA species (1.8 kb), was observed in all species.

EXAMPLE 5

The cDNA identified as coding for FAPα was subjected to more detailed analysis, starting with sequencing. The classic Sanger methodology, as set forth in Proc. Natl. Acad. Sci. USA 74: 5463–5467 (1977), was used to sequence both strands of the cDNA. Once this was secured, an amino acid sequence was deduced therefrom. This information is presented in SEQ ID NO: 1. The sequence was then compared to the known amino acid sequence of CD26 (Morimoto et al., J. Immunol. 143: 3430–3437 (1989)). FIG. 1 presents the comparison, using optimized sequence alignment. Any gaps in the comparison are indicated by asterisks, while identical amino acids are shown by dashes in the CD26 sequence. A hydrophobic, putative transmembrane sequence is double underlined, while potential N-glycosylation sites are single underlined.

The sequence analysis shows a 2815 base pair insert, wherein 2280 base pairs constitute the open reading frame. This ORF extends from-start codon ATG at nucleotide 209, to stop codon TAA at 2486.

The deduced polypeptide is 760 amino acids long, and has a molecular weight of 87,832. In contrast, N-Glycanase digested, immunopurified FAPα was reported to have an estimated $M_r$ of 75,000 on $NaDodSO_4$/PAGE (Rettig et al., Canc. Res. 53: 3327–3335 (1993)).

A GenBank data base search was carried out. The most closely related genes found were those encoding dipeptidyl peptidase IV homologues (DPPIV; EC 3.4.14.5), with human DPPIV (also known as T-cell activation antigen CD26), showing 51% nucleotide sequence identity, and 52% amino acid sequence identity.

The second set of related genes are human, rat, and bovine homologues of DPPX, a gene of unknown function widely expressed in brain and other normal tissues. The predicted human DPPX gene product shows about 30% amino acid sequence identity with FAPα and CD26. The FAPα molecule exhibits structural features typical of type II integral membrane proteins, including a large COOH-terminal extracellular domain, a hydrophobic transmembrane segment, and a short cytoplasmic tail. The putative extracellular domain contains five potential N-glycosylation sites, eleven cysteine residues (nine of which are conserved between FAPα and CD26), and three segments corresponding to highly conserved catalytic domains characteristic of serine proteases, such as DPPIV. These conserved sequences are presented in Table 2, which follows. Comparisons to DPPIV and DPPX were made via Morimoto et al., supra; Wada et al., Proc. Natl. Acad. Sci. USA 89: 197–201 (1992); Yokotani et al., Human Mol. Genet. 2: 1037–1039 (1993).

EXAMPLE 6

An additional set of experiments were carried out to determine whether FAPα related sequences are present in non-human species. To do so, human, mouse, and Chinese hamster genomic DNA was digested using restriction enzymes, and tested, via Southern blotting, using the 2.3 kb fragment, labelled with $^{32}P$, described supra. Hybridization was carried out using stringent washing conditions (0.1× SSC, 0.1% $NaDodSO_4$, 68° C.). Cross-hybridization was readily observed with both the mouse and hamster DNA, suggesting the existence of highly conserved FAPα homologues. In control experiments using the CD26 cDNA fragment described supra, no evidence of cross hybridization was observed.

EXAMPLE 7

The CD26 molecule shares a number of biochemical and serological properties with FAPβ, which is a previously described, FAPα associated molecule having a molecular weight of 105 KD, and is found on cultured fibroblasts and melanocytes (Rettig et al., Canc. Res. 53: 3327–3335 (1993)). Cotransfection experiments were carried out to determine whether FAPβ is a CD26 gene product. To test this, the same protocols were used which were used for transfection with pFAP.38 or pCD26, as described supra, but using the two vectors. The results presented supra showed that cotransfection efficiency was about 40% for each vector, so about 10–20% of cell should be cotransfected.

Following cotransfection, the COS-1 cells were Trans $^{35}S$-labeled, as described supra, then lysed, also as described supra.

The resulting cell extracts were separated on Con A SEPHAROSE, and the antigen (FAPα and/or CD26) were recovered in the Con A-bound fraction. The bound fraction was eluted with 0.25M α-D-mannopyranoside. Immunoprecipitation was then carried out, as described supra, and the precipitates were separated on $NaDodSO_4$/PAGE, also as discussed supra.

Those cells transfected only with pFAP.38 produced FAPα, but not FAPβ (determined from mAb F19 immunoprecipitates). They also produce no CD26 antigen (tested with EF-1). Those cells transfected with pCD26 alone produce CD26 but no FAPα. Cotransfectants produce CD26 and FAPα/FAPβ heteromers, as determined in the mAb F19 precipitates. This result provides direct evidence that FAPβ is a CD26 gene product.

EXAMPLE 8

It has been observed previously that some cultured human cell types coexpress FAPα and CD26, and show FAPα/

TABLE 2

Putative catalytic domains of FAPα, DPPIV and DPPX.

| | 624 | 702 | 734 |
|---|---|---|---|
| Human FAPα | .... WGWSYGG SEQ ID NO:4 | ........ GTADDNV SEQ ID NO:6 | ........ DQNHGLS SEQ ID NO:7 .... |
| Human DPPIV | .... WGWSYGG SEQ ID NO:4 | ........ GTADDNV SEQ ID NO:6 | ........ DEDHGIA SEQ ID NO:8 .... |
| Mouse DPPIV | .... WGWSYGG SEQ ID NO:4 | ........ GTADDNV SEQ ID NO:6 | ........ DEDHGIA SEQ ID NO:8 .... |
| Rat DPPIV | .... WGWSYGG SEQ ID NO:4 | ........ GTADDNV SEQ ID NO:6 | ........ DEDHGIA SEQ ID NO:8 .... |
| Yeast DPPIV | .... FGWSYGG SEQ ID NO:4 | ........ GTGDDNV SEQ ID NO:6 | ........ DSDHSIR SEQ ID NO:8 .... |
| Human DPPX | .... FGKDYGG SEQ ID NO:5 | ........ PTADEKI SEQ ID NO:9 | ......... DESHYFT SEQ ID NO:10 .... |
| Rat DPPX | .... FGKDYGG SEQ ID NO:5 | ........ ATADEKI SEQ ID NO:9 | ......... DESHYFH SEQ ID NO:10 .... |
| Bovine DPPX | .... FGKDYGG SEQ ID NO:5 | ........ ATADEKI SEQ ID NO:9 | ......... DESHYFS SEQ ID NO:10 .... |

CD26 heteromer formation. In vivo distribution patterns of FAPα and CD26, however, as determined in previous immunohistochemical studies, appeared to be-non-overlapping. (See Rettig et al., Proc. Natl. Acad. Sci. USA 85: 3110–3114 (1988); Garin-Chesa et al., Proc. Natl. Acad. Sci. USA 87: 7235–7329 (1990); Rettig et al., Canc. Res. 53: 3327–3335 (1993); Stein et al., in Knapp et al., eds. Leukocyte typing IV-white cell differentiation antigens, pp. 412–415 (Oxford University Press, N.Y. 1989), pp. 412–415; Möbious et al., J. Exp. Immunol. 74: 431–437 (1988)). In view of the potential significance of FAPα/CD26 coassociation, tissue distribution was reexamined, via side by side immunohistochemical staining of normal tissues and lesional tissues known to contain FAPAα$^+$ fibroblasts or FAPα$^+$ malignant cells.

To test the samples, they were embedded in OCT compound, frozen in isopentane precooled in liquid nitrogen, and stored at −70° C. until used. Five micrometer thick sections were cut, mounted on poly-L-lysine coated slides, air dried, and fixed in cold acetone (4° C., for 10 minutes). The sections were then tested with mAbs (10–20 ug/ml), using the well known avidin-biotin immmunoperoxidase method, as described by, e.g., Garin-Chesa et al., J. Histochem. Cytochem. 37: 1767–1776 (1989); Garin-Chesa et al., Proc. Natl. Acad. Sci. USA 87: 7235–7239 (1990); Rettig et al., Canc. Res. 53: 3327–3335 (1993); Garin-Chesa et al., Am. J. Pathol. 142: 557–567.

The results are shown in FIG. 2. Breast, colorectal, pancreas and lung carcinomas showed strong expression of FAPα and no CD26 was found (see FIGS. 2A and 2B). Five FAPα$^+$ sarcomas, including malignant fibrous histiocytoma (FIGS. 2C and 2D), were tested, and there was no expression of CD26. Examination of reactive fibroblasts of healing dermal wounds (FIGS. 2E, 2F), showed abundant expression of both FAPα and CD26. The three renal carcinomas tested (FIGS. 2G, 2H), showed expression of CD26 in malignant epithelium. FAPα was absent from malignant epithelial cells, and showed low expression in the stroma of these carcinomas.

EXAMPLE 9

A mammalian cell line, transfected with a FAPα encoding CDNA, was prepared.

Human embryonic kidney cell line 293 is well known and widely available from, e.g., the American Type Culture Collection.

Samples of 293 were maintained, in an incubator, at 37° C., in an atmosphere of 95% air, and 5% $CO_2$. The cells were cultured in a 50:50 mixture of Dulbecco's modified minimal essential medium and Ham's F12 medium, augmented with 10% fetal bovine serum, penicillin and streptomycin. Following the procedures described by Ustar et al., Eur. Mol. Biol. J. 1991, and/or Park et al., J. Biol. Chem. 169: 25646–25654 (1994), both of which are incorporated by reference, cDNA for FAPα (i.e., SEQ ID NO: 1), was transfected into the 293 cells. Details of the cDNA vector are provided, supra (pFAP.38). Transfectants were selected for resistance to antibiotics (200 ug/ml Geneticin), and were then maintained in selection medium, containing Geneticin.

Individual colonies of resistant cells were picked, grown to confluence in 6 well tissue culture plates, and were tested for FAPα expression in an immunofluorescence assay (IFA), using FAPα specific monoclonal antibody F19 as described supra.

Those colonies which expressed FAPα were expanded, and monitored by indirect IFA and cytofluorometric analysis, also as set forth, supra.

The IFAs were positive for the transfectants, referred to hereafter as cell line 293-FAP, but were negative for parental line 293.

EXAMPLE 10

In order to confirm that recombinant FAPα was, in fact, being produced, a series of immunoprecipitation experiments were carried out. These followed the methods of Park, et al., supra, and Rettig et al., Canc. Res. 53: 3327–3335 (1993), both of which are incorporated by reference. Essentially, $^{35}$[S] methionine labelled cell extracts were combined with monoclonal antibody F19, in the manner described supra. Precipitates were then boiled in extraction buffer and run on SDS-PAGE gels, using, as a negative control, mouse IgG1. Both cell line 293-FAP, and non transfected line 293 were tested. The results indicated clearly, that recombinant FAPα was produced by the transfected cell line 293-FAP. This was determined by immunoprecipitation analyses, using FAPα specific monoclonal antibody F19.

EXAMPLE 11

The ability to produce recombinant FAPα permitted further study of the molecule's properties. Specifically, given the structural features outlined in the prior examples, experiments were designed to determine if FAPα possesses enzymatic activities. The experiments were designed to test whether or not FAPα had extracellular matrix (ECM) protein degrading activity.

Extracts of 293-FAP cells were prepared, using an extraction buffer (0.15M NaCl, 0.05M Tris-HCl, pH 7.4, 10 mM $MgCl_2$, 1 percent Triton X-114), were cleared by centrifugation (4,000×g, 10 minutes at 40° C.), and phase partitioned at 37° C. for 10–20 minutes. This was followed by further centrifugation (4000×g, 20 minutes at 20–25° C.) Detergent phases were diluted with buffer (0.15M NaCl, 0.05M Tris-HCl pH 7.4, 5 mM $CaCl_2$, 5 mM $MgCl_2$, 0.75% Empigen BB), and separated on concanavalin A-Sepharose following Rettig et al., supra. Any concanavalin A bound fractions were eluted with 0.25M methyl-α-D-mannopyranoside in elution buffer 0.15M NaCl, 0.05M Tris-HCl, pH 7.4, 5 mM $CaCl_2$, 5 mM $MgCl_2$, 0.1% Triton X-100), mixed with zymography sample buffer (0.25M Tris-HCl, pH 6.8, 8% SDS, 40% glycerol, 0.01% bromophenol blue), at a 3:1 ratio, and used for further analysis.

Aliquots of sample were loaded onto polyacrylamide gels containing 0.1% of either of gelatin or casein. Electrophoresis was then carried out in a Biorad Mini-Protein II system, .at 20 mA constant current for 1.5–2 hours, until the bromophenol blue dye fronts of samples had reached the lower end of the gel. The gel was removed and incubated for one hour at 20–25° C. in a 2.5% aqueous solution of Triton X-100 on a rotary shaker. The Triton X-100 solution was decanted, and replaced with enzyme buffer (0.05M Tris-HCl, pH 7.5, 0.2M NaCl, 5 mM $CaCl_2$, 5 mM $MgCl_2$, 0.02% Brij 35). The gel was then incubated at 37° C. or 41° C., followed by staining or destaining at room temperature. Gels were stained with 0.5% of Coomassie Brilliant Blue G-250 in an aqueous solution of 30% methanol and 10% acetic acid for 15, 30, and 60 minutes, respectively. Subsequently, gels were incubated for 15 minutes in an aqueous solution of 30% $CH_3OH$ and 5% glycerol, followed by drying between sheets of cellophane.

Gelatinase activity was evaluated in accordance with Kleiner et al., Anal. Biochem. 218: 325–329 (1994), incorporated by reference in its entirety. This is a routine assay used to determine whether or not a protease capable of digesting gelatin is present. Labelled molecular weight standard were run on the same gels, under reducing conditions, for molecular weight determinations.

Proteolytic activity for defined amino acid sequence motifs were tested, using a well known membrane overlay assay. See Smith et al, Histochem. J. 24(9): 637–647 (1992), incorporated by reference. Substrates were Ala-Pro-7-amino-4-trifluoromethyl coumarin, Gly-Pro-7-amino-4-trifluoromethyl coumarin, and Lys-Pro-7-amino-4-trifluromethyl coumarin.

The results of these experiments are depicted, in part, in FIG. 3. This figure shows zymographic detection of gelatin degrading activity, in the cell extracts. See Kleiner et al., supra. A protein species of approximately 170 kilodaltons, as determined by SDS-PAGE, was observed to have gelatin degrading activity. This species, which was found in the 293-FAP cell line, but not in untransfected 293 cells, is thus identified as FAPα. The molecular weight is consistent with a dimer, i.e., a dimeric FAPα molecule.

The proteolytic activity described herein where gelatin is the substrate was not observed when casein was the substrate.

EXAMPLE 12

Further studies were then undertaken in order to characterize the 170 kD FAPα dimer further. Specifically, the experiments described in example 11 were repeated, except that 5% of 2-mercaptoethanol or 5 um iodoacetamide was added to the extracts prior to SDS-PAGE, or ethylenediamine N,N,N',N'-tetraacetic acid (10 mM) was added to the incubation buffer used for gelatin zymography. None of these treatments abolished the enzymatic activity. In contrast, heating at 100° C. for five minutes prior to SDS-polyacrylamide gel electrophoresis abolished the gelatin-degrading activity.

Further work, using a membrane overlay assay, described by, e.g., Smith et al., Histochem J. 24(9): 643–647 (1992), incorporated by reference, revealed that the FAPα dimers were able to cleave all of the Ala-Pro, Gly-Pro, and Lys-Pro dipeptides tested.

In further experiments, a fusion protein was produced which comprised the extracellular domains of both FAPα and murine CD8 proteins. This chimeric protein was produced in a baculovirus system in insect cells. The chimeric protein exhibited the same enzymatic activity as FAPα, using the model discussed supra.

The foregoing examples describe an isolated nucleic acid molecule which codes for fibroblast activating protein alpha ("FAPα"), as well as dimeric forms of the molecule, and uses thereof. The expression product of the sequence in COS-1 is a protein which, on SDS-PAGE of boiled samples, shows a molecular weight of about 88 kd. Deduced amino acid sequence, as provided in SEQ ID NO: 1, for one form of the molecule, yields a molecular weight of about 88 kd.

It should be noted that there is an apparent discrepancy in molecular weight in that the COS-1 isolate is glycosylated, while molecular weight from deduced amino acid sequences does not account for glycosylation. Membrane proteins are known to exhibit aberrant migration in gel systems, however, which may explain the difference observed here.

Also a part of the invention are chimeric and fusion proteins, which comprise a portion of FAPα which contain the molecule's catalytic domain, and additional, non FAPα components. The FAPα catalytic domain per se is also a part of the invention.

It is to be understood that, as described, FAPα may be glycosylated, with the type and amount of glycosylation varying, depending upon the type of cell expressing the molecule. The experiment described herein shows this. This is also true for the dimeric form of the molecule, first described herein, having a molecular weight of about 170 kilodaltons as determined by SDS-PAGE of unboiled samples.

The invention also comprehends the production of expression vectors useful in producing the FAPα molecule. In their broadest aspect, these vectors comprise the entire FAPα coding sequence or portions thereof, operably linked to a promoter. Additional elements may be a part of the expression vector, such as protein domains fused to the FAPα protein or protein portions ("fusion protein") genes which confer antibiotic resistance, amplifiable genes, and so forth.

The coding sequences and vectors may also be used to prepare cell lines, wherein the coding sequence or expression vector is used to transfect or to transform a recipient host. The type of cell used may be prokaryotic, such as E. coli, or eukaryotes, such as yeast, CHO, COS, or other cell types.

The identification of nucleic acid molecules such as that set forth in SEQ ID NO: 1 also enables the artisan to identify and to isolate those nucleic acid molecules which hybridize to it under stringent conditions. "Stringent condition" as used herein, refers to those parameters set forth supra, whereby both murine and hamster sequences were also identified. It will be recognized by the skilled artisan that these conditions afford a degree of stringency which can be achieved using parameters which vary from those recited. Such variance is apprehended by the expression "stringent conditions".

The ability of nucleic acid molecules to hybridize to complementary molecules also enables the artisan to identify cells which express FAPα, via the use of a nucleic acid hybridization assay. One may use the sequences described in the invention to hybridize to complementary sequences, and thus identify them. In this way, one can target mRNA, e.g., which is present in any cell expressing the FAPα molecule.

It is of course understood that the nucleic acid molecules of the invention are also useful in the production of recombinant FAPα, in both monomeric and dimeric form. The examples clearly show that host cells are capable of assembling the dimeric forms. The recombinant protein may be used, e.g., as a source of an immunogen for generation of antibodies akin to known mAb F19, and with the same uses. Similarly, the recombinant protein, and/or cells which express the molecule on their surface, may be used in assays to determine antagonists, agonists, or other molecules which interact with the FAPα molecule. Such molecules may be, but are not necessarily limited to, substrates, inhibiting molecules, antibodies, and so forth. This last feature of the invention should be considered in light of the observed structural resemblances to membrane bound enzymes. This type of molecule is associated with certain properties which need not be described in detail here. It will suffice to say that inhibition or potentiation of these properties as associated with FAPα is a feature of this invention. For example, one may identify substrates or the substrate for FAPα molecules, via the use of recombinant cells or recombinant FAPα per se. The substrates can be modified to improve their effect, to lessen their effect, or simply to label them with detectable signals so that they can be used, e.g., to identify cells which express FAPα. Study of the interaction of substrate and FAPα, as well as that between FAPα and any molecule whatsoever, can be used to develop and/or to identify agonists and antagonists of the FAPα molecule.

Also a feature of the invention are isolated, dimeric FAPα molecules which have a molecular weight of about 170 kilodaltons as determined by SDS-PAGE, their use as an enzymatic cleaving agent, and other uses as are described herein. Enzymatically active forms of FAPα may also be produced as recombinant fusion proteins, comprising the catalytic domain of FAPα and other protein domains with suitable biochemical properties, including secretory signals protease cleavage sites, tags for purification, and other elements known to the artisan. The fact that FAPα has particular properties, as described herein, permits the identification of the molecule on cells expressing them. In turn, because the FAPα molecule is associated with tumors and tumor stromal cells, targeting of FAPα with therapeutic agents serves as a way to treat cancerous or precancerous condition, by administering sufficient therapeutic agent to alleviate cancer load.

The experiments showing the proteolytic properties of FAPα lead to yet a further aspect of the invention. It is well known that proteases which degrade extracellular matrix, or "ECM" proteins have an important role on certain aspects of tumor growth, including their effect on tumor cell invasion, tumor blood vessel formation (i.e., neoangiogenesis), and tumor metastasis. Collagens are of special interest vis-a-vis the substrates of proteases, as the collagens are an important part of the ECM. The fact that FAPα digests ECM suggests a therapeutic role for inhibitors of the molecule. "Inhibitors", as used herein, refers to molecules which interfere with FAPα enzyme function. Specifically excluded from such inhibitors is the monoclonal antibody F19. This mAb is known to bind to but not inhibit the enzyme function of FAPα, and hence it is not an inhibitor. The art is quite well versed with respect to monoclonal antibodies which both bind to and inhibit enzymes. Further examples of such inhibitors would include, e.g., substrate derivatives, such as modified collagen molecules, which interfere with the active site or sites of the FAPα molecule. Other suitable inhibitors will be apparent to the skilled artisan, and need not be listed here. In addition, the recombinant FAPα proteins and FAPα-transfected cell lines described supra can be employed in an enzymatic screening assay, using the substrate described supra or other suitable substrates, to identify inhibitors from any compound library. One can identify such enzyme inhibitors by combining a molecule which has FAP enzyme activity, such as the dimeric molecules of the invention, including dimers of SEQ ID NO: 2, with a substrate for the molecule with the enzymatic activity, as well as a substance believed to be an inhibitor. Then, one determines the activity of the molecule with enzymatic activity on its substrate, in the presence of the substance believed to be enzyme inhibitor. If there is a decrease in activity when the test substance is present as compared to when it is absent, then the substance is an inhibitor.

Other aspects of the invention will be clear to the skilled artisan, and need not be set forth here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
      (A) LENGTH:     2815 Base pairs
      (B) TYPE:       nucleic acid
      (C) STRANDEDNESS: double
      (D) TOPOLOGY:   linear (xi) SEQUENCE DESCRIPTION: SEQ ID NO: 1:

```
AAGAACGCCC CCAAAATCTG TTTCTAATTT TACAGAAATC TTTTGAAACT TGGCACGGTA      60

TTCAAAAGTC CGTGGAAAGA AAAAAACCTT GTCCTGGCTT CAGCTTCCAA CTACAAAGAC     120

AGACTTGGTC CTTTTCAACG GTTTTCACAG ATCCAGTGAC CCACGCTCTG AAGACAGAAT     180

TAGCTAACTT TCAAAAACAT CTGGAAAAAT GAAGACTTGG GTAAAAATCG TATTTGGAGT     240

TGCCACCTCT GCTGTGCTTG CCTTATTGGT GATGTGCATT GTCTTACGCC CTTCAAGAGT     300

TCATAACTCT GAAGAAAATA CAATGAGAGC ACTCACACTG AAGGATATTT TAAATGGAAC     360

ATTTTCTTAT AAAACATTTT TTCCAAACTG GATTTCAGGA CAAGAATATC TTCATCAATC     420

TGCAGATAAC AATATAGTAC TTTATAATAT TGAAACAGGA CAATCATATA CCATTTTGAG     480

TAATAGAACC ATGAAAAGTG TGAATGCTTC AAATTACGGC TTATCACCTG ATCGGCAATT     540

TGTATATCTA GAAAGTGATT ATTCAAAGCT TTGGAGATAC TCTTACACAG CAACATATTA     600
```

-continued

```
CATCTATGAC CTTAGCAATG GAGAATTTGT AAGAGGAAAT GAGCTTCCTC GTCCAATTCA      660
GTATTTATGC TGGTCGCCTG TTGGGAGTAA ATTAGCATAT GTCTATCAAA ACAATATCTA      720
TTTGAAACAA AGACCAGGAG ATCCACCTTT TCAAATAACA TTTAATGGAA GAGAAAATAA      780
AATATTTAAT GGAATCCCAG ACTGGGTTTA TGAAGAGGAA ATGCTTCCTA CAAAATATGC      840
TCTCTGGTGG TCTCCTAATG GAAAATTTTT GGCATATGCG GAATTTAATG ATAAGGATAT      900
ACCAGTTATT GCCTATTCCT ATTATGGCGA TGAACAATAT CCTAGAACAA TAAATATTCC      960
ATACCCAAAG GCTGGAGCTA AGAATCCCGT TGTTCGGATA TTTATTATCG ATACCACTTA     1020
CCCTGCGTAT GTAGGTCCCC AGGAAGTGCC TGTTCCAGCA ATGATAGCCT CAAGTGATTA     1080
TTATTTCAGT TGGCTCACGT GGGTTACTGA TGAACGAGTA TGTTTGCAGT GGCTAAAAAG     1140
AGTCCAGAAT GTTTCGGTCC TGTCTATATG TGACTTCAGG GAAGACTGGC AGACATGGGA     1200
TTGTCCAAAG ACCCAGGAGC ATATAGAAGA AAGCAGAACT GGATGGGCTG GTGGATTCTT     1260
TGTTTCAAGA CCAGTTTTCA GCTATGATGC CATTTCGTAC TACAAAATAT TTAGTGACAA     1320
GGATGGCTAC AAACATATTC ACTATATCAA AGACACTGTG GAAATGCTA TTCAAATTAC      1380
AAGTGGCAAG TGGGAGGCCA TAAATATATT CAGAGTAACA CAGGATTCAC TGTTTTATTC     1440
TAGCAATGAA TTTGAAGAAT ACCCTGGAAG AAGAAACATC TACAGAATTA GCATTGGAAG     1500
CTATCCTCCA AGCAAGAAGT GTGTTACTTG CCATCTAAGG AAAGAAAGGT GCCAATATTA     1560
CACAGCAAGT TTCAGCGACT ACGCCAAGTA CTATGCACTT GTCTGCTACG GCCCAGGCAT     1620
CCCCATTTCC ACCCTTCATG ATGGACGCAC TGATCAAGAA ATTAAAATCC TGGAAGAAAA     1680
CAAGGAATTG GAAAATGCTT TGAAAAATAT CCAGCTGCCT AAAGAGGAAA TTAAGAAACT     1740
TGAAGTAGAT GAAATTACTT TATGGTACAA GATGATTCTT CCTCCTCAAT TTGACAGATC     1800
AAAGAAGTAT CCCTTGCTAA TTCAAGTGTA TGGTGGTCCC TGCAGTCAGA GTGTAAGGTC     1860
TGTATTTGCT GTTAATTGGA TATCTTATCT TGCAAGTAAG GAAGGGATGG TCATTGCCTT     1920
GGTGGATGGT CGAGGAACAG CTTTCCAAGG TGACAAACTC CTCTATGCAG TGTATCGAAA     1980
GCTGGGTGTT TATGAAGTTG AAGACCAGAT TACAGCTGTC AGAAAATTCA TAGAAATGGG     2040
TTTCATTGAT GAAAAAGAA TAGCCATATG GGGCTGGTCC TATGGAGGAT ACGTTTCATC      2100
ACTGGCCCTT GCATCTGGAA CTGGTCTTTT CAAATGTGGT ATAGCAGTGG CTCCAGTCTC     2160
CAGCTGGGAA TATTACGCGT CTGTCTACAC AGAGAGATTC ATGGGTCTCC AACAAAGGA      2220
TGATAATCTT GAGCACTATA AGAATTCAAC TGTGATGGCA AGAGCAGAAT ATTTCAGAAA     2280
TGTAGACTAT CTTCTCATCC ACGGAACAGC AGATGATAAT GTGCACTTTC AAAACTCAGC     2340
ACAGATTGCT AAAGCTCTGG TTAATGCACA AGTGGATTTC CAGGCAATGT GGTACTCTGA     2400
CCAGAACCAC GGCTTATCCG GCCTGTCCAC GAACCACTTA TACACCCACA TGACCCACTT     2460
CCTAAAGCAG TGTTTCTCTT TGTCAGACTA AAAACGATGC AGATGCAAGC CTGTATCAGA     2520
ATCTGAAAAC CTTATATAAA CCCCTCAGAC AGTTTGCTTA TTTTATTTTT TATGTTGTAA     2580
AATGCTAGTA TAAACAAACA AATTAATGTT GTTCTAAAGG CTGTTAAAAA AAAGATGAGG     2640
ACTCAGAAGT TCAAGCTAAA TATTGTTTAC ATTTTCTGGT ACTCTGTGAA AGAAGAGAAA     2700
AGGGAGTCAT GCATTTTGCT TTGGACACAG TGTTTTATCA CCTGTTCATT TGAAGAAAAA     2760
TAATAAAGTC AGAAGTTCAA AAAAAAAAAA AAAAAAAAA AAAGCGGCCG CTCGA           2815
```

(2) INFORMATION FOR SEQ ID NO: 2:

(i) SEQUENCE CHARACTERISTICS:
        (A) LENGTH: 760 amino acids

-continued (B) TYPE: amino acid
(D) TOPOLOGY: linear (xi) SEQUENCE DESCRIPTION: SEQ ID NO: 2:

```
Met Lys Thr Trp Val Lys Ile Val Phe Gly Val Ala Thr Ser Ala Val
 5                  10                  15
Leu Ala Leu Leu Val Met Cys Ile Val Leu Arg Pro Ser Arg Val His
 20                  25                  30
Asn Ser Glu Glu Asn Thr Met Arg Ala Leu Thr Leu Lys Asp Ile Leu
 35                  40                  45
Asn Gly Thr Phe Ser Tyr Lys Thr Phe Pro Asn Trp Ile Ser Gly
 50                  55                  60
Gln Glu Tyr Leu His Gln Ser Ala Asp Asn Ile Val Leu Tyr Asn
 65                  70                  75                  80
Ile Glu Thr Gly Gln Ser Tyr Thr Ile Leu Ser Asn Arg Thr Met Lys
 85                  90                  95
Ser Val Asn Ala Ser Asn Tyr Gly Leu Ser Pro Asp Arg Gln Phe Val
 100                 105                 110
Tyr Leu Glu Ser Asp Tyr Ser Lys Leu Trp Arg Tyr Ser Tyr Thr Ala
 115                 120                 125
Thr Tyr Tyr Ile Tyr Asp Leu Ser Asn Gly Glu Phe Val Arg Gly Asn
 130                 135                 140
Glu Leu Pro Arg Pro Ile Gln Tyr Leu Cys Trp Ser Pro Val Gly Ser
 145                 150                 155                 160
Lys Leu Ala Tyr Val Tyr Gln Asn Asn Ile Tyr Leu Lys Gln Arg Pro
 165                 170                 175
Gly Asp Pro Pro Phe Gln Ile Thr Phe Asn Gly Arg Glu Asn Lys Ile
 180                 185                 190
Phe Asn Gly Ile Pro Asp Trp Val Tyr Glu Glu Met Leu Pro Thr
 195                 200                 205
Lys Tyr Ala Leu Trp Trp Ser Pro Asn Gly Lys Phe Leu Ala Tyr Ala
 210                 215                 220
Glu Phe Asn Asp Lys Asp Ile Pro Val Ile Ala Tyr Ser Tyr Tyr Gly
 225                 230                 235                 240
Asp Glu Gln Tyr Pro Arg Thr Ile Asn Ile Pro Tyr Pro Lys Ala Gly
 245                 250                 255
Ala Lys Asn Pro Val Val Arg Ile Phe Ile Ile Asp Thr Thr Tyr Pro
 260                 265                 270
Ala Tyr Val Gly Pro Gln Glu Val Pro Val Pro Ala Met Ile Ala Ser
 275                 280                 285
Ser Asp Tyr Tyr Phe Ser Trp Leu Thr Trp Val Thr Asp Glu Arg Val
 290                 295                 300
Cys Leu Gln Trp Leu Lys Arg Val Gln Asn Val Ser Val Leu Ser Ile
 305                 310                 315                 320
Cys Asp Phe Arg Glu Asp Trp Gln Thr Trp Asp Cys Pro Lys Thr Gln
 325                 330                 335
Glu His Ile Glu Glu Ser Arg Thr Gly Trp Ala Gly Gly Phe Phe Val
 340                 345                 350
Ser Arg Pro Val Phe Ser Tyr Asp Ala Ile Ser Tyr Tyr Lys Ile Phe
 355                 360                 365
Ser Asp Lys Asp Gly Tyr Lys His Ile His Tyr Ile Lys Asp Thr Val
 370                 375                 380
Glu Asn Ala Ile Gln Ile Thr Ser Gly Lys Trp Glu Ala Ile Asn Ile
 385                 390                 395                 400
```

```
Phe Arg Val Thr Gln Asp Ser Leu Phe Tyr Ser Ser Asn Glu Phe Glu
405                 410                 415

Glu Tyr Pro Gly Arg Arg Asn Ile Tyr Arg Ile Ser Ile Gly Ser Tyr
420                 425                 430

Pro Pro Ser Lys Lys Cys Val Thr Cys His Leu Arg Lys Glu Arg Cys
435                 440                 445

Gln Tyr Tyr Thr Ala Ser Phe Ser Asp Tyr Ala Lys Tyr Tyr Ala Leu
450                 455                 460

Val Cys Tyr Gly Pro Gly Ile Pro Ile Ser Thr Leu His Asp Gly Arg
465                 470                 475                 480

Thr Asp Gln Glu Ile Lys Ile Leu Glu Glu Asn Lys Glu Leu Glu Asn
485                 490                 495

Ala Leu Lys Asn Ile Gln Leu Pro Lys Glu Glu Ile Lys Lys Leu Glu
500                 505                 510

Val Asp Glu Ile Thr Leu Trp Tyr Lys Met Ile Leu Pro Pro Gln Phe
515                 520                 525

Asp Arg Ser Lys Lys Tyr Pro Leu Leu Ile Gln Val Tyr Gly Gly Pro
530                 535                 540

Cys Ser Gln Ser Val Arg Ser Val Phe Ala Val Asn Trp Ile Ser Tyr
545                 550                 555                 560

Leu Ala Ser Lys Glu Gly Met Val Ile Ala Leu Val Asp Gly Arg Gly
565                 570                 575

Thr Ala Phe Gln Gly Asp Lys Leu Leu Tyr Ala Val Tyr Arg Lys Leu
580                 585                 590

Gly Val Tyr Glu Val Glu Asp Gln Ile Thr Ala Val Arg Lys Phe Ile
595                 600                 605

Glu Met Gly Phe Ile Asp Glu Lys Arg Ile Ala Ile Trp Gly Trp Ser
610                 615                 620

Tyr Gly Gly Tyr Val Ser Ser Leu Ala Leu Ala Ser Gly Thr Gly Leu
625                 630                 635                 640

Phe Lys Cys Gly Ile Ala Val Ala Pro Val Ser Ser Trp Glu Tyr Tyr
645                 650                 655

Ala Ser Val Tyr Thr Glu Arg Phe Met Gly Leu Pro Thr Lys Asp Asp
660                 665                 670

Asn Leu Glu His Tyr Lys Asn Ser Thr Val Met Ala Arg Ala Glu Tyr
675                 680                 685

Phe Arg Asn Val Asp Tyr Leu Leu Ile His Gly Thr Ala Asp Asp Asn
690                 695                 700

Val His Phe Gln Asn Ser Ala Gln Ile Ala Lys Ala Leu Val Asn Ala
705                 710                 715                 720

Gln Val Asp Phe Gln Ala Met Trp Tyr Ser Asp Gln Asn His Gly Leu
725                 730                 735

Ser Gly Leu Ser Thr Asn His Leu Tyr Thr His Met Thr His Phe Leu
740                 745                 750

Lys Gln Cys Phe Ser Leu Ser Asp
755                 760

(2) INFORMATION FOR SEQ ID NO: 3:

(i) SEQUENCE CHARACTERISTICS:
        (A) LENGTH:    766 amino acids
        (B) TYPE:      amino acid
        (D) TOPOLOGY:  linear (xi) SEQUENCE DESCRIPTION: SEQ ID NO: 3:
```

-continued

```
Met Lys Thr Pro Trp Lys Val Leu Leu Gly Leu Leu Ala Ala Ala
                  5                  10                  15
Leu Val Thr Ile Ile Thr Val Pro Val Leu Leu Asn Lys Gly Thr
             20                  25                  30
Asp Asp Ala Thr Ala Asp Ser Arg Lys Thr Tyr Thr Leu Thr Asp Tyr
         35                  40                  45
Leu Lys Asn Thr Tyr Arg Leu Lys Leu Tyr Ser Leu Arg Trp Ile Ser
 50                  55                  60
Asp His Glu Tyr Leu Tyr Lys Gln Glu Asn Asn Ile Leu Val Phe Asn
 65                  70                  75                  80
Ala Glu Tyr Gly Asn Ser Ser Val Phe Leu Glu Asn Ser Thr Phe Asp
                  85                  90                  95
Glu Phe Gly His Ser Ile Asn Asp Tyr Ser Ile Ser Pro Asp Gly Gln
                 100                 105                 110
Phe Ile Leu Leu Glu Tyr Asn Tyr Val Lys Gln Trp Arg His Ser Tyr
             115                 120                 125
Thr Ala Ser Tyr Asp Ile Tyr Asp Leu Asn Lys Arg Gln Leu Ile Thr
         130                 135                 140
Glu Glu Arg Ile Pro Asn Asn Thr Gln Trp Val Thr Trp Ser Pro Val
145                 150                 155                 165
Gly His Lys Leu Ala Tyr Val Trp Asn Asn Asp Ile Tyr Val Lys Ile
                 170                 175                 180
Glu Pro Asn Leu Pro Ser Tyr Arg Ile Thr Trp Thr Gly Lys Glu Asp
             185                 190                 195
Ile Ile Tyr Asn Gly Ile Thr Asp Trp Val Tyr Glu Glu Glu Val Phe
         200                 205                 210
Ser Ala Tyr Ser Ala Leu Trp Trp Ser Pro Asn Gly Thr Phe Leu Ala
 215                 220                 225
Tyr Ala Gln Phe Asn Asp Thr Glu Val Pro Leu Ile Glu Tyr Ser Phe
230                 235                 240                 245
Tyr Ser Asp Glu Ser Leu Gln Tyr Pro Lys Thr Val Arg Val Pro Tyr
                 250                 255                 260
Pro Lys Ala Gly Ala Val Asn Pro Thr Val Lys Phe Phe Val Val Asn
             265                 270                 275
Thr Asp Ser Leu Ser Ser Val Thr Asn Ala Thr Ser Ile Gln Ile Thr
         280                 285                 290
Ala Pro Ala Ser Met Leu Ile Gly Asp His Tyr Leu Cys Asp Val Thr
     295                 300                 305
Trp Ala Thr Gln Glu Arg Ile Ser Leu Gln Trp Leu Arg Arg Ile Gln
310                 315                 320                 325
Asn Tyr Ser Val Met Asp Ile Cys Asp Tyr Asp Glu Ser Ser Gly Arg
                 330                 335                 340
Trp Asn Cys Leu Val Ala Arg Gln His Ile Glu Met Ser Thr Thr Gly
             345                 350                 355
Trp Val Gly Arg Phe Arg Pro Ser Glu Pro His Phe Thr Leu Asp Gly
         360                 365                 370
Asn Ser Phe Tyr Lys Ile Ile Ser Asn Glu Glu Gly Tyr Arg His Ile
     375                 380                 385
Cys Tyr Phe Gln Ile Asp Lys Lys Asp Cys Thr Phe Ile Thr Lys Gly
390                 395                 400                 405
Thr Trp Glu Val Ile Gly Ile Glu Ala Leu Thr Ser Asp Tyr Leu Tyr
                 410                 415                 420
Tyr Ile Ser Asn Glu Tyr Lys Gly Met Pro Gly Gly Arg Asn Leu Tyr
```

-continued

```
                425                 430                 435
Lys Ile Gln Leu Ser Asp Tyr Thr Lys Val Thr Cys Leu Ser Cys Glu
            440                 445                 450
Leu Asn Pro Glu Arg Cys Gln Tyr Tyr Ser Val Ser Phe Ser Lys Glu
455                 460                 460
Ala Lys Tyr Tyr Gln Leu Arg Cys Ser Gly Pro Gly Leu Pro Leu Tyr
465                 470                 475                 480
Thr Leu His Ser Ser Val Asn Asp Lys Gly Leu Arg Val Leu Glu Asp
                485                 490                 495
Asn Ser Ala Leu Asp Lys Met Leu Gln Asn Val Gln Met Pro Ser Lys
            500                 505                 510
Lys Leu Asp Phe Ile Ile Leu Asn Glu Thr Lys Phe Trp Tyr Gln Met
            515                 520                 525
Ile Leu Pro Pro His Phe Asp Lys Ser Lys Lys Tyr Pro Leu Leu Leu
            530                 535                 540
Asp Val Tyr Ala Gly Pro Cys Ser Gln Lys Ala Asp Thr Val Phe Arg
545                 550                 555                 560
Leu Asn Trp Ala Thr Tyr Leu Ala Ser Thr Glu Asn Ile Ile Val Ala
                565                 570                 575
Ser Phe Asp Gly Arg Gly Ser Gly Tyr Gln Gly Asp Lys Ile Met His
            580                 585                 590
Ala Ile Asn Arg Arg Leu Gly Thr Phe Glu Val Glu Asp Gln Ile Glu
            595                 600                 605
Ala Ala Arg Gln Phe Ser Lys Met Gly Phe Val Asp Asn Lys Arg Ile
            610                 615                 620
Ala Ile Trp Gly Trp Ser Tyr Gly Gly Tyr Val Thr Ser Met Val Leu
625                 630                 635                 640
Gly Ser Gly Ser Gly Val Phe Lys Cys Gly Ile Ala Val Ala Pro Val
                645                 650                 655
Ser Arg Trp Glu Tyr Tyr Asp Ser Val Tyr Thr Glu Arg Tyr Met Gly
            660                 665                 670
Leu Pro Thr Pro Glu Asp Asn Leu Asp His Tyr Arg Asn Ser Thr Val
            675                 680                 685
Met Ser Arg Ala Glu Asn Phe Lys Gln Val Glu Tyr Leu Leu Ile His
            690                 695                 700
Gly Thr Ala Asp Asp Asn Val His Phe Gln Gln Ser Ala Gln Ile Ser
705                 710                 715                 720
Lys Ala Leu Val Asp Val Gly Val Asp Phe Gln Ala Met Trp Tyr Thr
                725                 730                 735
Asp Glu Asp His Gly Ile Ala Ser Ser Thr Ala His Gln His Ile Tyr
            740                 745                 750
Thr His Met Ser His Phe Ile Lys Gln Cys Phe Ser Leu Pro
            755                 760                 765
```

(2) INFORMATION FOR SEQ ID NO: 4:

(i) SEQUENCE CHARACTERISTICS:
        (A) LENGTH:   7 amino acids
        (B) TYPE:     amino acid
        (D) TOPOLOGY: linear (ix) FEATURE:
        (D) OTHER INFORMATION:   The first Xaa is either Trp or Phe.

(xi) SEQUENCE DESCRIPTION:    SEQ ID NO: 4:

Xaa Gly Trp Ser Tyr Gly Gly

-continued

5

(2) INFORMATION FOR SEQ ID NO: 5:

(i) SEQUENCE CHARACTERISTICS:
        (A) LENGTH:   7 amino acids
        (B) TYPE:     amino acid
        (D) TOPOLOGY: linear (xi) SEQUENCE DESCRIPTION: SEQ ID NO: 5:

Phe Gly Lys Asp Tyr Gly Gly
              5

(2) INFORMATION FOR SEQ ID NO: 6:

(i) SEQUENCE CHARACTERISTICS:
        (A) LENGTH:   7 amino acids
        (B) TYPE:     amino acid
        (D) TOPOLOGY: linear (ix) FEATURE:
        (D) OTHER INFORMATION: Xaa is either Ala or Gly (xi) SEQUENCE DESCRIPTION: SEQ ID NO: 6:

Gly Thr Xaa Asp Asp Asn Val
              5

(2) INFORMATION FOR SEQ ID NO: 7:

(i) SEQUENCE CHARACTERISTICS:
        (A) LENGTH:   7 amino acids
        (B) TYPE:     amino acid
        (D) TOPOLOGY: linear (xi) SEQUENCE DESCRIPTION: SEQ ID NO: 7:

Ala Gln Asn His Gly Leu Ser
              5

(2) INFORMATION FOR SEQ ID NO: 8:

(i) SEQUENCE CHARACTERISTICS:
        (A) LENGTH:   7 amino acids
        (B) TYPE:     amino acid
        (D) TOPOLOGY: linear (ix) FEATURE:
        (D) OTHER INFORMATION:
            The first Xaa is Glu or Ser.  When the first Xaa is Glu,
            the second Xaa is Gly and the third is Ala.  When the
            first Xaa is Ser, the second Xaa is Ser, and the third
            Xaa is Arg.

(xi) SEQUENCE DESCRIPTION: SEQ ID NO: 8:

Asp Xaa Asp His Xaa Ile Xaa
              5

(2) INFORMATION FOR SEQ ID NO: 9:

(i) SEQUENCE CHARACTERISTICS:
        (A) LENGTH:   7 amino acids
        (B) TYPE:     amino acid
        (D) TOPOLOGY: linear (ix) FEATURE:
        (D) OTHER INFORMATION:
            Xaa is Pro or Ala.

(xi) SEQUENCE DESCRIPTION: SEQ ID NO: 9:

Xaa Thr Ala Asp Glu Lys Ile
              5

```
(2) INFORMATION FOR SEQ ID NO: 10:

(i) SEQUENCE CHARACTERISTICS:
        (A) LENGTH:    7 amino acids
        (B) TYPE:      amino acid
        (D) TOPOLOGY:  linear (ix) FEATURE:
        (D) OTHER INFORMATION:
            Xaa is Thr, His or Ser.

(xi) SEQUENCE DESCRIPTION: SEQ ID NO: 10:

Asp Glu Ser His Tyr Phe Xaa
                  5
```

We claim:

1. An isolated protein consisting of:
   (i) an extracellular domain of an FAPα protein, the amino acid sequence of which is set forth in SEQ ID NO: 1, and
   (ii) at least one domain of a non FAPα protein.

2. The Isolated protein of claim 1, wherein said non FAPα protein is a CD8 protein.

3. The isolated protein of claim 1, wherein said at least one domain of a non FAPα protein is an extracellular domain of a CD8 protein.

4. The isolated protein of claim 1, wherein said protein is a chimeric protein.

5. The isolated protein of claim 1, wherein said protein is a fusion protein.

* * * * *